(12) United States Patent
Tan (10) Patent No.: US 9,101,497 B2
(45) Date of Patent: Aug. 11, 2015

(54) EXTERNAL PROSTHETIC PENILE DEVICE

(76) Inventor: Kah Peow Tan, Singapore (SG)

( * ) Notice: Subject to any disclaimer, the term of this patent is extended or adjusted under 35 U.S.C. 154(b) by 539 days.

(21) Appl. No.: 13/447,523

(22) Filed: Apr. 16, 2012

(65) Prior Publication Data

US 2012/0271101 A1   Oct. 25, 2012

Related U.S. Application Data

(60) Provisional application No. 61/477,088, filed on Apr. 19, 2011.

(51) Int. Cl.
*A61F 5/41* (2006.01)
*A61F 2/50* (2006.01)
*A61H 19/00* (2006.01)
*A61H 23/02* (2006.01)

(52) U.S. Cl.
CPC *A61F 2/50* (2013.01); *A61H 19/32* (2013.01); *A61H 19/44* (2013.01); *A61H 19/50* (2013.01); *A61H 23/02* (2013.01); *A61F 2002/5001* (2013.01); *A61H 2201/0107* (2013.01)

(58) Field of Classification Search
CPC .................. A61H 19/44; A61H 19/34; A61H 2201/0153; A61H 23/0263; A61H 19/32; A61H 23/02; A61H 19/40; A61H 23/00; A61H 19/50; A61H 19/30; A61F 2/26; A61F 5/41; A61F 2005/411; A61F 2005/415; A61F 2005/412; A61F 2006/048

USPC ........................................ 600/38–40; 601/70
See application file for complete search history.

(56) References Cited

U.S. PATENT DOCUMENTS

| | | | | |
|---|---|---|---|---|
| 5,573,499 | A * | 11/1996 | McAllister | 601/70 |
| 2009/0301496 | A1 * | 12/2009 | Reddy et al. | 128/830 |
| 2012/0136203 | A1 * | 5/2012 | Weng et al. | 600/38 |

* cited by examiner

*Primary Examiner* — Christine H Matthews
(74) *Attorney, Agent, or Firm* — John Alumit (57) ABSTRACT

An external prosthetic penile device includes a substantially cylindrical structure having openings at its proximal end and a distal end. The substantially cylindrical structure includes a tubular channel that extends and tapers within the substantially cylindrical structure from the proximal end to the distal end. The tubular channel connects said proximal and distal end openings in a fluid connection. The opening at the proximal end includes a funnel, said funnel having a substantially conical mouth, wherein said substantially conical mouth has a circumference that is adapted to rest substantially against a pubic region surrounding a human's genitals. The circumference is also dimensioned to at least substantially encompass the genitals when the circumference is fitted against the pubic region. The substantially cylindrical structure is configured to resemble a flaccid human penis such that the distal opening corresponds to the external urethral orifice.

20 Claims, 4 Drawing Sheets

EXTERNAL PROSTHETIC PENILE DEVICE

CROSS-REFERENCE TO RELATED APPLICATION

This application claims the benefit of provisional patent application No. 61/477,088 filed on Apr. 19, 2011.

FEDERALLY SPONSORED RESEARCH

Not Applicable

SEQUENCE LISTING OR PROGRAM

Not Applicable

STATEMENT REGARDING COPYRIGHTED MATERIAL

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

BACKGROUND

The present invention relates to the field of prosthetic penile devices, and in particular, to an external penile prosthetic device that (i) simulates the presence of an actual penis, (ii) allows for urination while standing and (iii) simulates an erected penis thereby allowing sexual intercourse.

A micropenis is defined as a normally structured penis that is below the normal size range for an infant. Normally, the length of a penis of a male newborn ranges between 2.8-4.2 centimeters (cm) with a circumference of 0.9 to 1.3 cm. This measurement is taken by stretching the penis and measuring the penis from its tip to the base thereof. A penis of less than 1.9 cm is usually considered to be a micropenis. Micropenises occur due to hormonal disorders. Specifically, micropenises result where there is an abnormal level of the hormones involved in the development of the sexual organs and typically involves the pituitary gland or the hypothalamus ("*Congenital Micropenis: Long-Term Medical, Surgical, and Psychosexual Follow-Up of Individuals Raised Male or Female*" Hormone Research (2001) 56, pp. 3-11).

A typical treatment for those born with a micropenis takes place shortly after birth and/or around puberty. Such treatment typically involves hormones to stimulate further penile growth. A more extreme form of treatment that is carried out is a sex reassignment surgery where the micropenis and testes are removed and an artificial vagina is constructed. For adult men having a micropenis, hormonal treatment is not a viable option as by then, such treatment has little or no effect in promoting penile growth. Instead, the adult has to either live with the condition or attempt the more drastic measure of having a sex reassignment surgery, which is more complicated amongst adults.

In the 1990 s, controversy from such sex reassignment surgeries resulted in many hospitals discarding the practice. Poor outcomes were reported in both infants and adults who undergo sex reassignment procedures. Risks included infection, postoperative pain, and dissatisfaction with anticipated results. Studies found that such patients end up requiring more counseling in the long run (Lobe et al, "*The complications of surgery for intersex: changing patterns over two decades*" (1987) 22 (7) Journal of Pediatric Surgery 651-2).

In addition to the psychological and physical health risks, the financial cost of sex reassignment surgeries is generally prohibitive. For example, the cost of a male having a micropenis undergoing a sex reassignment surgery to become a female is estimated to cost up to US$25,000. With the decline of surgery as an option, many of those having the condition of micropenises have simply elected to lead their lives as best they can. In this regard, the micropenis condition can have a profound impact on a man's self-esteem. In particular, those having a micropenis find the practice of urinating while standing to be an almost impossible task. Accordingly, such persons with micropenises began to turn increasingly to prosthetic or artificial penises to overcome what is considered primarily to be an issue of self-esteem.

As mentioned, the cost of sex reassignment surgeries is prohibitively expensive. The same applies for females undergoing a sex reassignment surgery to become a male. For such females, the cost of a sex reassignment surgery is even more prohibitive with estimates hitting as high as US$50,000. One of the reasons for the substantially higher cost is largely due to the difficulty in surgically constructing a penis, a process known as phalloplasty. A major step in phalloplasty is the lengthening of the urethra. Common complications that arise during this step include as follows:

Urinary fistula (hole) requiring perineal urethrostomy;
Urinary fistula (hole) with conservative treatment;
Urinary retention (from stenosis or narrowing of the new urethra);
(Erectile) prosthesis change (from complications); and
(Erectile) prosthesis explantation (removal of the prosthesis without replacement).

Apart from the above complications, it is reported that on average, 25% of post-op patients (women who underwent a sex reassignment surgery to become men) suffered from one or more of the following complications:

Loss of the phallus from either disease or blood supply issues;
Cephalic vein thrombosis (blood clot);
Arterial ischaemia (shortage of blood supply);
Infection;
Distal limited necrosis (death of parts of the penis); and
Haematoma (bruising).

In view of the above, another group of individuals who are also reliant on artificial penises are transsexuals or transgendered persons (hereafter in this context collectively referred to as "transsexuals") who are unable, either due to medical or financial reasons, to undergo a complete or successful sex reassignment procedure that includes phalloplasty.

Both the above-mentioned groups, i.e. those having micropenises and transsexuals, essentially either do not have a male reproductive organ or have one that is perceived to be insufficient. In relying on artificial or prosthetic penile devices, the aforesaid groups require a device that is capable of satisfying the following requirements:

i. Creating a visual presence, i.e. a forming a sufficient bulge in a person's attire to give the impression that said person is sexually well-endowed (referred to hereafter as "packing");
ii. Allowing for urination while standing; and
iii. Being capable of performing sexual intercourse.

Apart from the above requirements, in view of the possible risks that can arise from surgery, a solution that is non-invasive is also preferable.

Presently there are many prosthetic penile devices commercially available. United States patent application US2006/0063971A1 ("the '971 Application") discloses a prosthetic penile device. However, the purpose of the prosthetic penile device disclosed herein is solely for the purpose of enhancing the sexual stimulation during intercourse [see paragraph 6, '971 Application]. There is no mention made of the prosthetic penile attachment permitting any urinary function, nor is the prosthetic penile attachment disclosed as being intended for everyday use to provide a "packing" function.

U.S. Pat. No. 5,842,970 ("the '970 Patent") discloses an external penile prosthetic adapted to be worn on the groin and pubic areas of a user. The users include the following groups of persons:
  i. Those who can have an erection but nevertheless feel that their penises are not sufficiently large,
  ii. Those who have partial erections,
  iii. Those who cannot obtain any erection at all, and
  iv. Those who do not have a penis at all.

The default position of the device disclosed in this patent is that of an erect human penis (see column 4, lines 28-33, '970 Patent). Accordingly, this external penile prosthetic device, as with the previously discussed prosthetic penis, only serves to enhance the sexual stimulation during intercourse and does not provide any means for aiding in urination nor is it suited for everyday use given its default erect position.

Finally, a PCT application published as WO2010/079795A1 ("the '795 Application") discloses a prosthetic penis that bears an appearance similar to that of a male reproductive organ. The published specification is in the Japanese language. However, according to an English translation of the abstract, the prosthetic penis is meant for persons "having no male sex organs" and as such, the prosthetic penis is intended to "sufficiently fulfil the original functions of male sex organs." In this regard, it is disclosed that the prosthetic penis includes a urinary tract (designated by reference numeral 8) that runs through the shaft of the penis (designated by reference numeral 4) and that the urinary tract (8) has to be connected to a user's urethral opening. However, there is no mention of the use of the organ for sexual intercourse and furthermore, the connection of the urinary tract (8) to the user's urethral opening may be considered to be at the very least, invasive in nature (see the English abstract, '795 Application). Also, the default erect appearance would preclude this device from being used for any "packing" function.

As can be seen from the solutions reviewed above, apart from WO2010/079795, such solutions concerning artificial or prosthetic penises that have been promulgated are directed towards solving the problem of erectile dysfunction, penile enlargement and further stimulation during intercourse, i.e. problems typically associated with males having regularly sized penises. The solutions discussed above are not directed towards assisting those having a micropenis or a lack of a male sexual organ.

As such, despite the above-mentioned attempts at providing adequate treatment or surgical options to those with micropenises and transsexuals, and despite the multitude of prosthetic penises available, there is still a need for an external prosthetic penile device that provides adequate packing, allows for urination to take place while standing up; and caters for the performance of sexual intercourse. In addition, there is also a need for such a device that is non-invasive, comfortable to wear, easy to use and cost-effective to produce. In this respect, an external prosthetic penile device, as defined in the claims appended below, overcomes the above-mentioned difficulties.

SUMMARY

The external prosthetic penile device includes a substantially cylindrical structure having openings at its proximal end and a distal end. The substantially cylindrical structure includes a tubular channel within. The tubular channel extends and tapers within the substantially cylindrical structure from the proximal end to the distal end (also referred to herein as the tapered tubular channel). The tubular channel connects said proximal and distal end openings (also referred to as the proximal opening and distal opening, respectively) in a fluid connection. The opening at the proximal end includes a funnel, said funnel having a substantially conical mouth. The substantially conical mouth has a circumference that is adapted to rest substantially against a pubic region surrounding a human's genitals. The circumference is also dimensioned to at least substantially encompass the genitals when the circumference is fitted against the pubic region. The substantially cylindrical structure is configured to resemble a flaccid human penis such that the opening at the distal end corresponds to the external urethral orifice.

The funnel itself has a substantially conical mouth that is integrally connected to the proximal opening such that the funnel and the proximal opening are in fluid connection. As mentioned, the substantially conical mouth has a circumference that is dimensioned to at least substantially encompass existing human genitalia. In other words, the circumference of the substantially conical mouth and the depth of the conical mouth, when placed over human genitalia (male or female), has the effect of substantially covering said human genitalia. Generally, although it is preferable that the entire genitals of the person should be covered, at the very least, the urethra of either the male or female ought to be covered by the substantially conical mouth. In males, that would mean that at least the tip portion of the penis should be within the substantially conical mouth or preferably within the proximal opening. In females, at least the region of the vulva into which the urethra opens should be covered within the substantially conical mouth, although covering the entire vagina is preferable.

In one embodiment, the tubular channel that tapers from the proximal end to the distal end may be at least substantially co-axially located within the substantially cylindrical structure. As with the previous embodiment, the tapered tubular channel terminates at the distal opening of the substantially cylindrical structure.

This arrangement of the funnel with respect to the substantially cylindrical structure therefore has the effect of allowing for the following to take place:
  (i) Urination into the substantially conical mouth of the funnel (or directly into the tapered tubular chamber), and
  (ii) Channeling of the urine from the funnel into the tapered tubular channel (which is located within the substantially cylindrical structure) and out of the opening of the substantially cylindrical structure for disposal.

Not only is the aesthetic design of the device intended to simulate a human penis, but the manner in which urine is discharged is also intended to mimic the natural manner by which urination takes place. In this respect, it is common knowledge that in carrying out urination while standing, a certain pressure is exerted by the body in order that the stream of urine exits the penis at a particular velocity such that the stream of urine is discharged away from the body in what may be described as a substantially parabolic curve.

The present device does not incorporate any pump for increasing the velocity at which the urine is discharged. However, as mentioned, the design and inclusion of the tapered tubular channel permits the urine to exit the opening at what would appear to be in a pressurised manner as well by relying on the principle of conservation of mass. The principle states that mass cannot be created nor destroyed. Accordingly, the mass of urine entering the substantially conical mouth of the funnel under constant pressure equates to the mass of urine being discharged at the opening. This is better illustrated with reference to Bernoulli's equation as follows:

$$p_1 - p_2 = \frac{1}{2}\rho(V_2^2 - V_1^2)$$

Assuming a constant fluid flow, i.e. constant pressure, the above equation reduces to the following:

$$A_1V_1 = A_2V_2$$

Where $A_x$ denotes the cross-sectional area of the tube within which a liquid is flowing and $V_x$ denotes the velocity at which the liquid is flowing.

Thus, it is clear that in order for the above-mentioned mathematical relationship to be satisfied, as the cross-sectional area A decreases (as it does in a tapered tube), i.e. $A_1 > A_2$, then it follows that $V_2 > V_1$, i.e. the velocity of the fluid in the narrower portion of any tube is higher than the velocity of the fluid at the broader portion of the tube. The fluid stream being discharged is then likely to follow what might be described as a parabolic path.

In an exemplary embodiment where the device of the present invention is used with respect to a male person, the diameter of the tapered tubular channel extending from the proximal end should preferably be sufficient to fit over a human penis, and where applicable, it may even be dimensioned to fit a micropenis specifically. In being fitted to a human penis, the initial portion of the tapered tubular channel will fit the human penis like a sheath. In other words, the human penis may be inserted into the tapered tubular channel (in a tight-fit) to the extent that the circumference of the substantially conical mouth at least rests substantially against a pubic surface surrounding the genitalia of a male person. In general, the circumference of the substantially conical mouth may be adapted in terms of contouring to rest substantially against the complementary contours of the pubic surface surrounding the genitalia of a person. In this particular exemplary embodiment, this results in the human penis being in fluid connection with the tapered tubular channel thereby allowing urine to be discharged via the tubular channel and opening.

It is to be noted that although the above exemplary embodiment has been described in relation to a human male, the device may also be used by a female, in particular, a transsexual or transgendered person who may not have undergone a complete sex reassignment surgery. Such a person may still retain female genitalia while appearing as a male in all other aspects. In this regard, the device is to be used as described above except that the circumference of the substantially conical mouth will encompass at least the urethra or preferably the entire vagina. During urination, the substantially conical mouth of the funnel will direct the stream of urine to the tapered tubular channel.

When the device is used as described in the above exemplary embodiment, and in consideration of the aforesaid mathematical relationship, the tapered tubular channel allows the stream of urine being discharged from the prosthetic penile device to mimic that as discharged from an actual human penis, i.e. the stream of urine will also follow what may be described as a parabolic path.

In one embodiment, the distal end of the substantially cylindrical structure and the funnel are substantially homogeneously interfaced together. By so doing, it is preferred that there be no seam or joint visible between the two parts. It is preferable that the funnel should transition seamlessly into the substantially cylindrical structure.

This substantially homogenous interface may be achieved by manufacturing the device using conventional moulding techniques including, but not limited to, injection moulding, compression moulding and blow moulding, for example.

The device may be made from a material such as a silicone blend. Examples of such silicone blends include, but are not limited to, those typically used to manufacture medical prosthetics. General examples of such silicone blends include, but are not limited to, similar blends of silicone that are used to manufacture breast implants, or silicone blends used in Hollywood special facial effects makeup studios, so they are non-toxic to human contact. Specific examples include, but are not limited to, Silicone A-595 and silicone elastomers such as EFX Series Part A manufactured by SO Incorporated, for example.

In yet another embodiment, the device may further include a portion at least extending from the circumference of the substantially conical mouth. This portion may be shaped, coloured, positioned and textured to resemble a pair of human testicles. This may be preferable where the device is intended to visually resemble the actual human penis.

In a further embodiment, the device may be adapted to be attached, secured and/or held in place to the human pubic region by means of a harness or strap. Alternatively, in another embodiment, the circumference of the substantially conical mouth may further include a flange upon which medical glue can be applied to secure the device to the pubic region of a person via said flange. The flange may be also formed integrally with the funnel so that the device is formed as a single piece.

Generally, it is preferred that the device be dimensioned to resemble that of an at least average-sized flaccid human penis, such that a sufficient bulge is produced when the device is used under any article of clothing. This feature may be seen as fulfilling the "packing" requirement as described previously. In this regard, the device could well be made in various sizes in order to cater to individual preferences as well as to different body structures inherently present across different racial groups. The importance of this feature of the present invention is that for man having a micropenis, or for transsexuals, the visual presence of an average-sized or normal penis with respect to the public at large can help in boosting their self-esteem.

In yet another embodiment of the invention, the device accordingly may further include a removable erector rod. The removable erector rod is tapered such that it is capable of insertion into the correspondingly tapered tubular channel. Upon insertion of the removable erector rod a tight fit may result between the erector rod and surface of the tapered tubular channel.

The purpose of the removable erector rod is to enable the device to appropriately mimic a human penis capable of engaging in sexual intercourse. Accordingly, the removable erector rod is of sufficient rigidity such that the insertion of the removable erector rod into the tapered tubular channel stiffens the flaccid substantially cylindrical structure to a degree of rigidity. The degree of rigidity provided mimics that of a human phallus capable of undertaking sexual intercourse.

In an embodiment where the device is intended for use with a transsexual, i.e. a women who does not have a penis, the removable erector rod may include a flange at its thicker end such that the flange at least substantially contacts the second end of the funnel when the removable erector rod is fully inserted into the tapered tubular channel. The flange would then prevent the removable erector rod from being inserted further into the tapered tubular channel.

Alternatively, where the device is intended to be used by a male person having a penis or micropenis, the removable erector rod may also include a flange at its thicker end. However, in this alternative embodiment, the flange is dimensioned such that it can be inserted, i.e. enter into the tapered tubular channel up to a fixed distance. Upon reaching the point where the diameter of the tapered tubular channel prevents the flange from being inserted further, a fixed distance (or space) is created within the tapered tubular channel between the flange and the second end of the funnel, i.e. the start of the stem. It is within this space that the male user may insert his penis or micropenis, as the case may be, in order to engage in sexual intercourse using the device.

In a further embodiment, the removable erector may be adapted to provide oscillatory or vibratory motion while inserted in the tapered tubular channel. The mechanical motion stated above may be achieved by the use of suitable motors and/or actuators including, but not limited to, micro motors, stepper motors, linear actuators, pneumatic actuators, hydraulic actuators and piezoelectric actuators.

In yet another embodiment, the removable erector rod may be curved to the extent that it is capable of approximately contacting a Gräfenberg Spot (more commonly referred to as a G-spot) of a human female during sexual intercourse. The Gräfenberg Spot is typically located one to three inches (2.5 to 7.6 cm) up the front (anterior) vaginal wall between the vaginal opening and the urethra and is a sensitive area that is part of the female prostate. Accordingly, the flexibility of the substantially cylindrical structure permits it to be manipulated, via the insertion of an appropriately shaped removable erector rod, such that it is capable of contacting and stimulating the Gräfenberg Spot during sexual intercourse.

As the aim of the present invention is to provide a prosthetic penis that is capable of providing sufficient packaging, urination while standing capability and sexual functionality, in another embodiment of the invention, it is preferred that the device be adapted such that its surface is textured and coloured to resemble that of an actual human penis.

The following illustrations and accompanying description serve to further aid in the understanding and clarity of the invention. However, it should be noted that the scope of the invention is by no means limited to the exemplary embodiments described and illustrated hereafter.

DETAILED DESCRIPTION OF THE DRAWINGS

Figure 1:
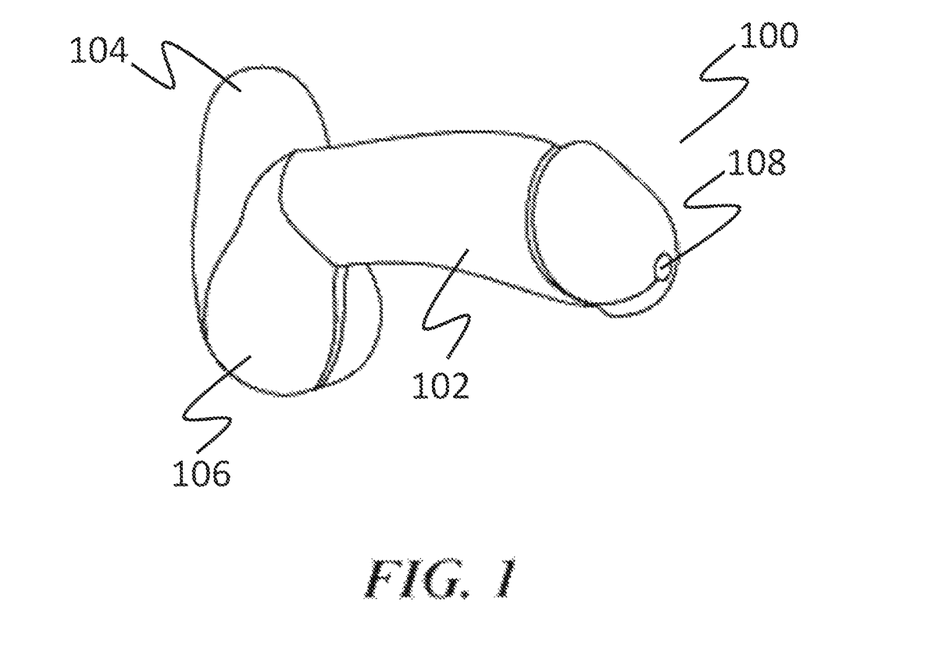
FIG. 1 is an illustration of an embodiment of the prosthetic penile device.

FIG. 1 is an illustration of an embodiment of an external prosthetic penile device 100. The device 100 is designed such that it resembles a male human penis. The device has a penis (shaft) 102 that has an opening 108 at its tip. The opening 108 is intended to mimic or replicate an external urethral orifice. The shaft 102 is homogenously connected to a funnel 104. Funnel 104 includes a portion 106 that mimics or replicates a pair of testicles. Funnel 104 is also shaped such that it is adapted to rest at least substantially flush against the pubic region surrounding a person's genitals.

It should be noted that the size of the device may vary according to an individual's preferences, although the configuration will always remain the same, i.e. the presence of a funnel 104, a mock up of a pair of testicles 106, a shaft 102 and an opening that mimics an external urethral orifice.

Figure 2:
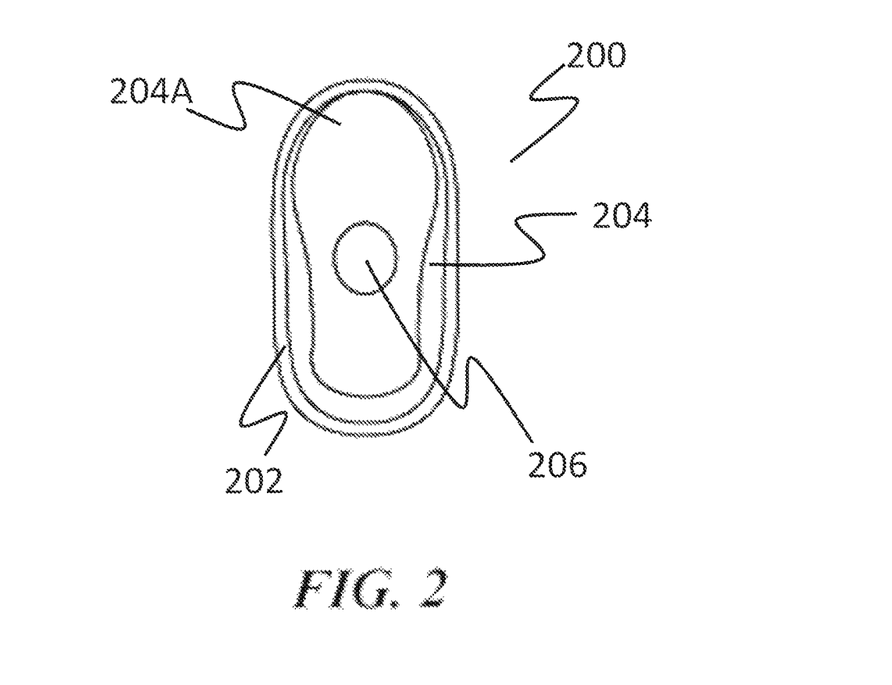
FIG. 2 is an illustration of a back view of an embodiment of the prosthetic penile device.

FIG. 2 is an illustration of a back view 200 of an embodiment of an external prosthetic penile device. Back view 200 shows funnel 104. The funnel 104 includes a circumference 202. Circumference 202 is the portion of the funnel that is specifically adapted to rest against pubic regions of users.

Within funnel 104, is a substantially conical mouth 204 that extends in a tapering fashion (or inwardly sloping manner) across regions 204A till it reaches the proximal opening 206. The inward sloping regions 204 and 204A are essential for channeling fluid, i.e. urine, from the genitals of a user to proximal opening 206.

For a male user, the diameter of proximal opening 206 is sufficient to accommodate therein, in a push-fit or tight-fit manner, a human penis. The human penis may be a micro penis or an average-sized penis. Depending upon the size of the penis to be accommodated, the diameter of the proximal opening 206 may be varied accordingly. For a female user, the entire circumference 202, which rests against the pubic region of a user, may be sufficiently dimensioned such that it is capable of at least encompassing the region of the female genitals from which urine is discharged from, i.e. at least the female urethra.

Figure 3:
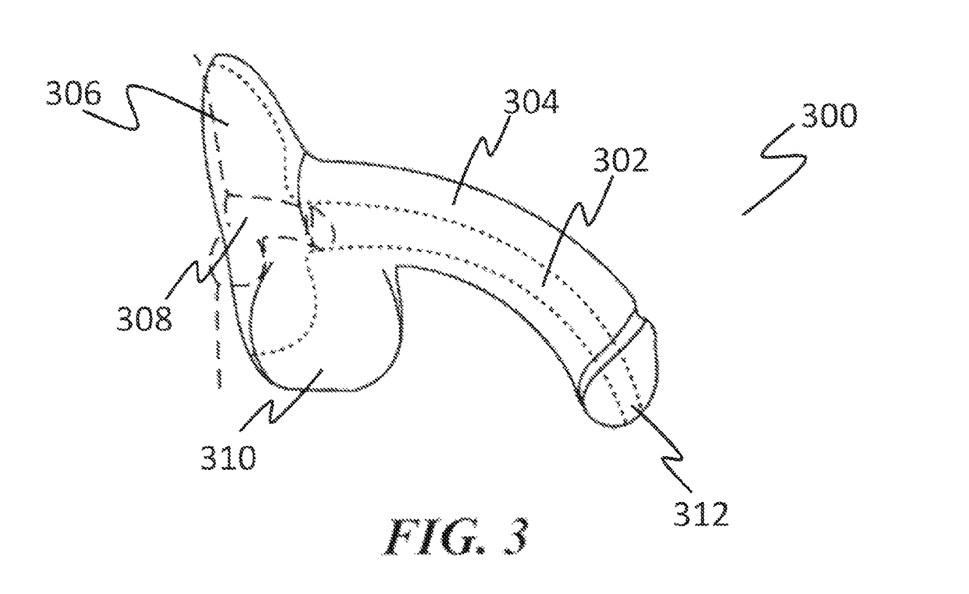
FIG. 3 is an illustration of the embodiment of the device of FIG. 1 as fitted onto a user having a micropenis.

FIG. 3 is an illustration of the embodiment 300 of the device of FIG. 1 as fitted onto a user having a micropenis 308. As shown in the illustration, the micropenis 308 enters into the tapered tubular channel 302 during the affixing process. This enables the micropenis 308 to be affixed via a tight-fit and in fluid connection with the tapered tubular channel 302. As such, when urine is discharged from the micropenis 308, it will flow via the tapered tubular channel 302 and out the distal opening 312.

As can be observed from the embodiment 300, the penis 304 itself is flaccid, as a normal penis would be. Also, the funnel 306, which extends from and is in fluid connection with the proximal opening, i.e. the start of the tapered tubular channel, is sufficiently large enough to encompass the entire genital area of the user. Although it is sufficient that at least the penis be within the funnel, it is preferable that the entire genitals of the user be encompassed. This is because upon the device being affixed, the circumference of the funnel 306 will be able to rest against the surrounding pubic region to ensure a more secure and comfortable fit. Also, with portion 310, which is designed to resemble a pair of testicles present, a proper fit is helpful towards ensuring that the "packing" provided by the device when worn under clothing would appear normal.

Figure 4:
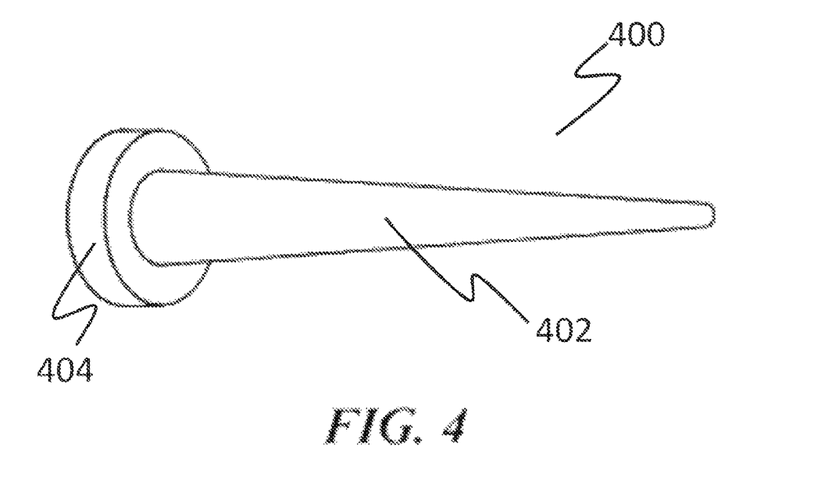
FIG. 4 is an illustration of an embodiment of a removable erector rod.

FIG. 4 is an illustration of an embodiment of a removable erector rod 400. As illustrated, the rod 400 that has a tapered body 402 extending from its base 404. The base 404 may be a flange. The use and function of the removable erector rod are further described below with respect to FIG. 5 and FIG. 6.

Figure 5:
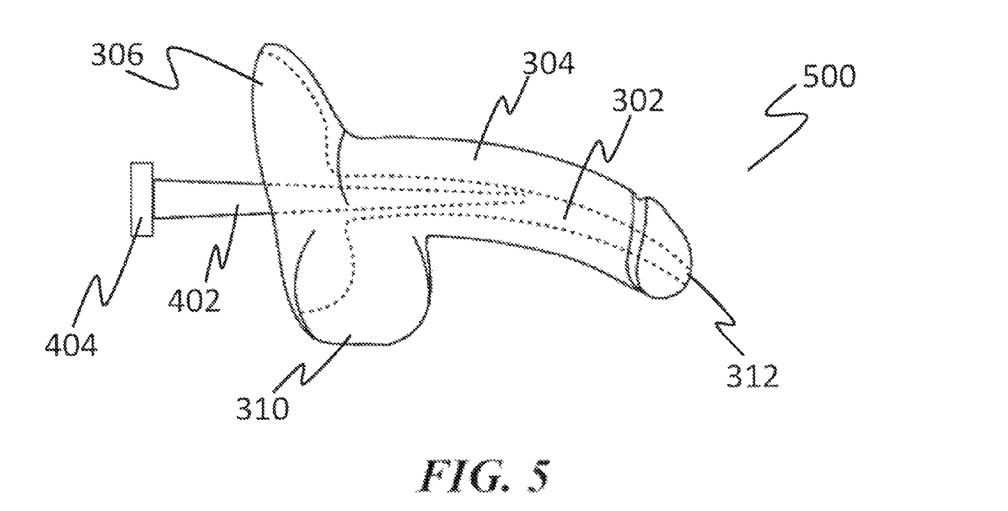
FIG. 5 and FIG. 6 are illustrations showing the removable erector rod of FIG. 4 in use.
Figure 6:
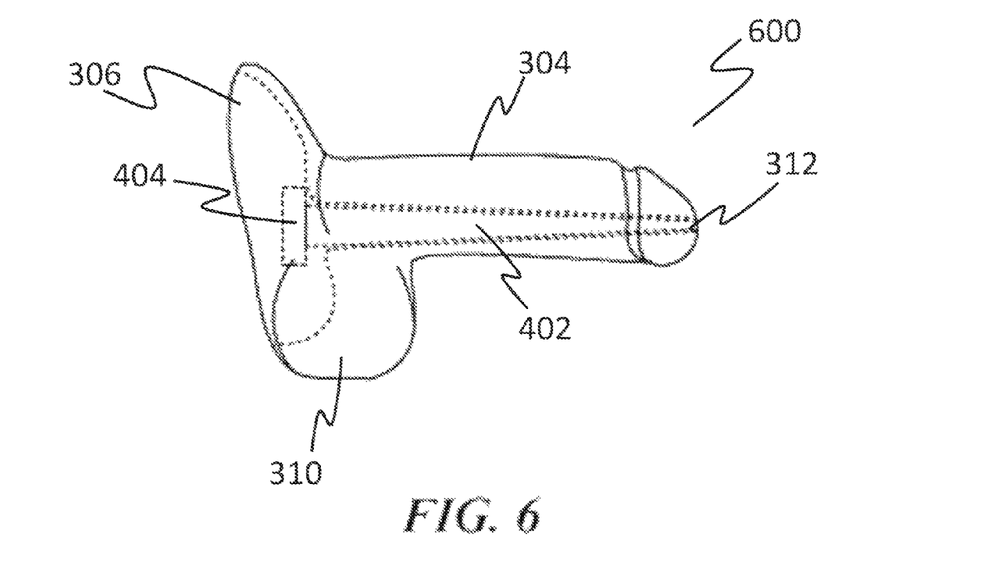

FIG. 5 and FIG. 6 are illustrations showing the removable erector rod 400 of FIG. 4 in use. FIG. 5 shows the partial insertion of the erector rod 400 into the device 100. FIG. 6 shows the complete insertion of the erector rod 400 into the device 100.

FIG. 5, the removable erector rod 400 is partially inserted. The tapered body 402 is inserted into the tapered tubular channel 502. The insertion results in a partial stiffening of the penis 504 such that the penis 504 rises, losing some of its curvature as compared to the penis 304 in FIG. 3. All the other parts of the device, i.e. 302, 304, 306, 310 and 312 are as previously described.

Turning to FIG. 6, once the tapered body 402 of the removable erector rod 400 has been fully inserted into the device 100, the penis 304 further stiffens and in so doing, it also loses more of its curvature as compared to FIG. 5. At this point, the penis 304 may be considered to be mimicking an erect human male penis sufficient to use to engage in sexual intercourse.

As also shown, when the removable erector rod 400 is fully inserted into the tapered tubular channel 302 (not shown in FIG. 6), the base 404 of the erector rod 400 is in at least substantial contact with proximal opening. The base 404 is shown to be larger than the proximal opening such that it prevents the erector rod 400 from being further inserted into the tapered tubular channel 302. Accordingly, in this exemplary embodiment 600, after the erector rod is inserted fully, there is no further room in the tapered tubular channel 302. As such, this embodiment is only suitable for use by a transgendered or transsexual person. In such a case, the funnel 306 would at least cover the urethra of the person, or preferably the entire vagina.

Figure 7:
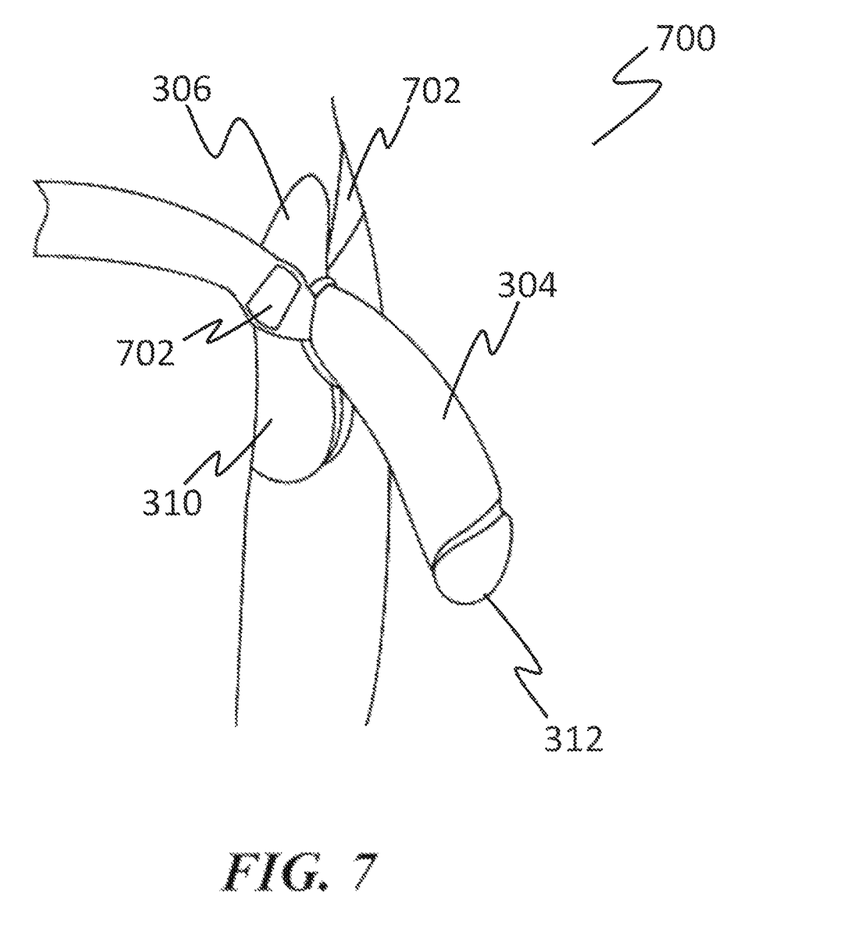
FIG. 7 is an illustration showing an embodiment of the device as fitted to a user via a harness.

FIG. 7 is an illustration showing an embodiment 700 of the device as fitted to a user via a harness 702. The user may be a male or female. As shown, the flaccid stated of the penis 304 indicates that the erector rod is not being used. Also, the circumference of the funnel 306 encompasses the entire genitals of the user and this ensures a comfortable and snug fit between the device and the user's pubic region. It should be noted that the circumference of the funnel may be contoured to custom-fit the pubic region of a user according to dimensions and measurements taken.

As mentioned earlier, the above description of the exemplary embodiments of the present invention merely serve to aid in the understanding of the underlying principle behind the invention. The present invention is not to be construed as being limited to the illustrated embodiments but rather, to the extent as defined in the claims that follow.

What is claimed is:

1. An external prosthetic penile device comprising: a substantially cylindrical structure having openings at its proximal end and a distal end, wherein the substantially cylindrical structure comprises a tubular channel that extends and tapers within the substantially cylindrical structure from the proximal end to the distal end, the tubular channel connecting said proximal and distal end openings in a fluid connection; wherein the opening at the proximal end comprises a funnel, said funnel comprising: a substantially conical mouth, wherein said substantially conical mouth has a circumference that is adapted to rest substantially against a pubic region surrounding a human's genitals, and is dimensioned to at least substantially encompass the genitals when the circumference is fitted against the pubic region; and wherein said substantially cylindrical structure is configured to resemble a flaccid human penis such that the opening at the distal end corresponds to an external urethral orifice.

2. The device according to claim 1, wherein the tubular channel that extends and tapers from the opening at the proximal end to the opening at the distal end is at least substantially co-axial to the substantially cylindrical structure.

3. The device according to claim 1, wherein the circumference of the substantially conical mouth is substantially elliptical in shape.

4. The device according to claim 1, wherein the circumference of the substantially conical mouth is contoured to fit to contours of a user's pubic region.

5. The device according to claim 1, wherein the proximal opening is larger than the distal opening.

6. The device according to claim 1, wherein the circumference of the substantially conical mouth of the funnel and a circumference of the substantially cylindrical structure are substantially homogeneously interfaced together.

7. The device according to claim 1, wherein the funnel further comprises a portion at least extending from the circumference of the substantially conical mouth, wherein the portion is shaped to resemble a pair of human testicles.

8. The device according to claim 1, wherein the device is made from a silicone blend selected from a group consisting of Silicone A-595 and EFX Series Part A.

9. The device according to claim 1, wherein the opening at the proximal end is dimensioned to fit over and at least partially accommodate a human penis within the tubular channel when the circumference of the substantially conical mouth rests substantially against the pubic region of a male person, such that the human penis is in fluid connection with the tubular channel, thereby allowing urine to be discharged via the tubular channel and opening at the distal end.

10. The device according to claim 1, wherein the circumference of the substantially conical mouth of the funnel is dimensioned to fit over and at least partially encompass a human vagina within the funnel when the circumference of the substantially conical mouth rests substantially against the pubic region of a female person, such that the at least partially encompassed vagina is in fluid connection with the tubular channel, thereby allowing urine to be discharged via the tubular channel and opening at the distal end.

11. The device according to claim 1, wherein the device is configured to be attached to the pubic region by means of a harness or strap.

12. The device according to claim 1, where the circumference of the substantially conical mouth comprises a flange upon which medical glue is applied to secure the device to the pubic region of a person via said flange.

13. A device according to claim 1, wherein the device is dimensioned such that a sufficient bulge is produced when the device is used under any article of clothing.

14. The device according to claim 1, the device further comprising a removable erector rod, wherein the removable erector rod is tapered such that it is capable of insertion into the tubular channel that extends and tapers from the proximal end to the distal end.

15. The device according to claim 14, wherein the removable erector rod comprises a flange having a fixed diameter at one end of the removable erector rod, said diameter of the flange being larger than that of the proximal opening such that the flange cannot be inserted into the tubular channel.

16. The device according to claim 14, wherein the removable erector rod comprises a flange having a fixed diameter at one end of the removable erector rod, wherein the diameter of the flange is equivalent to a diameter of the tubular channel at a point between the proximal end and the distal end, such that the flange can be inserted into the tubular channel up to the point where the diameter of the flange equals the diameter of the tubular channel.

17. The device according to claim 16, wherein the point is of a fixed distance from the proximal opening, said fixed distance being sufficient to accommodate a human penis.

18. The device according to claim 14, wherein the removable erector rod is of sufficient rigidity such that insertion of the removable erector rod into the tubular channel stiffens the substantially cylindrical structure to a degree of rigidity, said degree of rigidity mimicking that of a human phallus capable of undertaking sexual intercourse.

19. The device according to claim 14, wherein the removable erector rod is adapted to provide oscillatory or vibratory motion while inserted in the tubular channel.

20. The device according to claim 14, wherein the removable erector rod is curved to an extent that it is capable of approximately contacting a Grafenberg Spot of a human female during sexual intercourse.

* * * * *